United States Patent
Mir Heidari

(10) Patent No.: US 9,068,217 B2
(45) Date of Patent: Jun. 30, 2015

(54) METHOD AND DEVICE FOR DETERMINING MICROBIAL POLLUTION LEVEL IN DIFFERENT ENVIRONMENTS AND PROCESSES

(71) Applicant: Saeed Mir Heidari, Irvine, CA (US)

(72) Inventor: Saeed Mir Heidari, Irvine, CA (US)

( * ) Notice: Subject to any disclaimer, the term of this patent is extended or adjusted under 35 U.S.C. 154(b) by 0 days.

(21) Appl. No.: 14/523,934

(22) Filed: Oct. 26, 2014

(65) Prior Publication Data

US 2015/0044762 A1    Feb. 12, 2015

(30) Foreign Application Priority Data

Feb. 25, 2014   (WO) .................. PCT/IB2014/059225

(51) Int. Cl.
| | |
|---|---|
| *C12M 1/28* | (2006.01) |
| *C12Q 1/04* | (2006.01) |
| *C12M 1/12* | (2006.01) |
| *C12Q 1/08* | (2006.01) |
| *C12M 1/24* | (2006.01) |
| *C12M 1/26* | (2006.01) |
| *C12M 1/30* | (2006.01) |
| *C12M 1/00* | (2006.01) |

(52) U.S. Cl.
CPC .................. *C12Q 1/04* (2013.01); *C12M 33/02* (2013.01); *C12M 23/04* (2013.01); *C12Q 1/08* (2013.01); *C12M 23/38* (2013.01); *C12M 23/20* (2013.01); *C12M 23/08* (2013.01); *C12M 33/04* (2013.01)

(58) Field of Classification Search
CPC ...... C12M 23/04; C12M 23/08; C12M 23/20; C12M 23/38; C12M 25/14; C12M 33/02; C12M 33/04; C12M 41/36; C12Q 1/04; C12Q 1/06; C12Q 1/08; C12Q 1/20; C12Q 1/24; G01N 33/56911

USPC ..................... 435/33, 40, 287.6, 287.9, 309.1
See application file for complete search history.

(56) References Cited

U.S. PATENT DOCUMENTS

| | | | | |
|---|---|---|---|---|
| 3,849,256 | A * | 11/1974 | Linder ....................... | 435/287.7 |
| 4,591,556 | A * | 5/1986 | Saxholm ...................... | 435/33 |
| 5,026,491 | A * | 6/1991 | Haack et al. .................. | 507/237 |
| 6,627,413 | B1 | 9/2003 | Buri et al. | |
| 2006/0121601 | A1* | 6/2006 | Backman et al. .......... | 435/287.9 |
| 2009/0035808 | A1* | 2/2009 | Zoch et al. .................... | 435/39 |
| 2009/0305336 | A1 | 12/2009 | Swanson | |

FOREIGN PATENT DOCUMENTS

| | | | |
|---|---|---|---|
| WO | WO 9002169 | A1 * | 3/1990 |
| WO | WO 2007028649 | A1 * | 3/2007 |

OTHER PUBLICATIONS

Oxoid Limited: "Oxoid Dip Slide", Thermo Fischer Scientific Inc., XP002725554. Retrieved from the Internet (Jun. 10, 2014): URL: http://www.oxoid.com/uk/blue/prod_detail/prod_detail.asp?pr=ds0147.*

* cited by examiner

*Primary Examiner* — William H Beisner
(74) *Attorney, Agent, or Firm* — Barry Choobin; Patent 360

(57) ABSTRACT

The present invention provides a device for detecting aerobic bacteria, anaerobic bacteria and fungi in a targeted material which comprises of a plurality sided slide, and a vial, wherein a first side of said plurality sided slide is coated with a first predetermined medium for aerobic bacteria growth and a second side of said plurality sided slide is coated with a second predetermined medium for fungal (mold and yeast) growth, and wherein at the bottom of said vial a third predetermined medium is embedded to determine a level of presence of anaerobic bacteria.

13 Claims, 4 Drawing Sheets

METHOD AND DEVICE FOR DETERMINING MICROBIAL POLLUTION LEVEL IN DIFFERENT ENVIRONMENTS AND PROCESSES

CROSS REFERENCE TO RELATED APPLICATIONS

The present invention claim priority of a PCT application PCT/IB2014/059225 filed 25 Feb. 2014.

BACKGROUND OF THE INVENTION

Microbial growth is a problem in many different places such as hospitals, slaughter houses, chicken farms, dairy farms and factories. Microbes can contaminate solid waste, water, fuel, petrochemical products and industrial fluids. Microbial presence and their metabolic by-products can result in health problems and change in the physical and chemical properties of their host environment. These biomaterials in some systems block the fluid transfer pipes and furthermore can cause chemical deterioration in such systems which results in poor performance and may require costly maintenance. An example is metal-working fluid emulsions or coolants in metal working machines where high microbial growth will cause instability, corrosion, odour and sludge formation resulting in undesirable performance by the fluid. The microbes growing in metalworking fluids could be aerobic bacteria such as *Pseudomonas, Bacillus* and *Staphylococcus*, Anaerobic Bacteria such as *Desulfovibrio* and fungus such as *Penicillium* spp. and *Candid*.

Monitoring the microbial load in fluids will help in evaluation of the quality and efficiency of biocides used or the bio-stability of the materials in the fluid. There are different methods to determine the measure of microbial load such as plate count, direct microscopic count, ATP measurement and enzyme activity, which all are common methods in microbiology but are both time consuming and costly. The aforesaid methods will usually require a microbiologist or a person familiar with microbiological methods and also a laboratory setting. In many situations, having a user-friendly device for microbial evaluation in a short period of time on site and without having any knowledge of microbiology would be a great advantage.

OBJECTS OF THE EMBODIMENTS

The primary object of the embodiments herein is to provide a device for detecting aerobic bacteria, anaerobic bacteria and fungi in a targeted material which comprises of a plurality sided slide, and a vial, wherein a first side of said plurality sided slide is coated with a first predetermined medium for aerobic bacteria growth and a second side of said plurality sided slide is coated with a second predetermined medium for fungal (mold and yeast) growth, and wherein at the bottom of said vial a third predetermined medium is embedded to determine a level of presence of anaerobic bacteria.

Another object of the embodiments herein is to provide a device for detecting aerobic bacteria, anaerobic bacteria and fungi in a targeted material which comprises of a plurality sided slide, wherein the slide comprises a needle.

Yet another object of the embodiments herein is to provide a device for detecting aerobic bacteria, anaerobic bacteria and fungi in a targeted material which comprises of a plurality sided slide, wherein said slide further comprises a sealing cap to seal the vial to prevent any contamination before and after its use.

Yet another embodiment of the present invention is to provide a device for detecting aerobic bacteria, anaerobic bacteria and fungi in a targeted material, wherein said vial comprises an opening area for inserting said slide.

Yet another embodiment of the present invention is to provide a device for detecting aerobic bacteria, anaerobic bacteria and fungi in a targeted material, wherein said slide further comprises a third and more sides which is coated with other mediums for determination of various aerobic bacteria and fungi.

Yet another embodiment of the present invention is to provide a device for detecting aerobic bacteria, anaerobic bacteria and fungi in a targeted material, wherein said first side is coated with medium for molds and yeasts growth.

Yet another embodiment of the present invention is to provide a device for detecting aerobic bacteria, anaerobic bacteria and fungi in a targeted material, wherein said second side is coated with medium for aerobic bacteria growth.

Yet another embodiment of the present invention is to provide a device for detecting aerobic bacteria, anaerobic bacteria and fungi in a targeted material, wherein said vial contains a special medium for SRB bacteria.

Yet another embodiment of the present invention is to provide a device for detecting aerobic bacteria, anaerobic bacteria and fungi in a targeted material, wherein medium is deposited at the bottom of the vial, and wherein a predetermined amount of paraffin wax or flexible polymers is deposited on top of said medium to create an anaerobic environment.

Yet another embodiment of the present invention is to provide a device for detecting aerobic bacteria, anaerobic bacteria and fungi in a targeted material, wherein said device configured to estimate the number of anaerobic bacteria by detecting changes of attributes comprising colors at the bottom of the vial.

Yet another embodiment of the present invention is to provide a device for detecting aerobic bacteria, anaerobic bacteria and fungi in a targeted material, wherein said device is configured to estimated level of yeasts by comparing a number of colonies grown on the second side for fungi with a first chart provided for yeasts.

Yet another embodiment of the present invention is to provide a device for detecting aerobic bacteria, anaerobic bacteria and fungi in a targeted material, wherein said device is configured to estimated level of mold by comparing a number of colonies grown on the second side with a second chart provided for mold.

Yet another embodiment of the present invention is to provide a device for detecting aerobic bacteria, anaerobic bacteria and fungi in a targeted material, wherein said device is configured to estimated level of aerobic bacteria by comparing a number of colonies grown on the first side with a third chart provided for aerobic bacteria.

Yet another embodiment of the present invention is to provide a device for detecting aerobic bacteria, anaerobic bacteria and fungi in a targeted material, wherein said plurality sided slide comprises geometrical lumps on the sides of the slide to prevent medium from detaching and cracking.

Yet another embodiment of the present invention is to provide a device for detecting aerobic bacteria, anaerobic bacteria and fungi in a targeted material, wherein the device is configured to detect different strains of microorganisms in different environments by altering the medium.

Yet in another embodiment of the present invention, the needle attached to the slide is moveable.

In another embodiment of the present invention, the needle can be triggered towards anaerobic the medium by the way of pressing a trigger button arranged on top of the sealing cap without contaminating the needle.

Yet in another embodiment of the present invention, there is not a fissure in the center of the anaerobic part coating layer.

Yet in another embodiment of the present invention, the upper portion of the slide is in a bendable form and material.

Yet in another embodiment, slide can have various shapes, for example curved shape, triangular shape so to accommodate a more efficient delivery system for the samples to the tip of the needle.

Yet in another embodiment of the present invention the device can be used easily and without need for trained operator and laboratory equipment.

Yet in another embodiment of the present invention the device functions in a reliable and rapid manner.

Yet in another embodiment of the present invention the device is highly safe for the operator.

Yet in another embodiment of the present invention the device is Economical to use. Yet in another embodiment of the present invention the device is designed to be used for liquids, semi-solid and hard surfaces.

Yet in another embodiment of the present invention the device separate sections for determination of aerobic bacteria, yeasts, molds, and SRB.

Yet in another embodiment of the present invention very small amounts of sample is needed to perform the test.

Yet in another embodiment of the present invention minimal contact with contaminants outside the sample occurs.

Yet in another embodiment of the present invention the device provides an easy recognition and estimation of microbes.

Yet in another embodiment of the present invention the device provides Simultaneous determination of aerobic bacteria, molds, yeasts.

SUMMARY OF INVENTION

The present invention is a method and a design of a vial for determination of microbial pollution level in different environments and processes. This vial consists of 3 sections for simultaneous detection and evaluation of aerobic bacteria, fungi (yeast and mold) and anaerobic bacteria (sulphate reducing bacteria) growth. In the present invention, aerobic bacteria and fungi population count is based on colony forming on the sides of a slide and comparing them with their presented provided chart. Estimation of the level of anaerobic bacteria growth and population is based on a circular formation at the bottom of the vial which is also compared with a given provided chart. The microbial counts are reported as CFU/ml (Colony Forming Unit per Milliliter).

The present invention provides a suitable device to conduct easy and quick microbial tests in various environments and processes. The device comprises of a plurality sided slide, preferably 2 sided, and a vial. A first side of said plurality sided slide is coated with a first predetermined medium for aerobic bacteria growth and a second side of said plurality sided slide is coated with a second predetermined medium for fungal (mold and yeast) growth. In special cases, a third and more sides of the plural sided slide could be coated with other medium for determination of various aerobic bacteria and fungi. At the bottom of said vial a third predetermined medium is embedded to determine a level of presence of anaerobic bacteria. The slide is inserted into said vial and said slide further comprises a sealing cap to seal the vial to prevent any contamination before and after its use. The media for microbial growth on the slide are prepared under sterile condition and its coated surfaces are free of any contaminant. This tool can be used to test solid surfaces, semisolid materials and fluids based and water containing materials. The different parts of the device are described in the following sections.

BRIEF DESCRIPTION OF THE DRAWINGS

The other objects, features and advantages will occur to those skilled in the art from the following description of the preferred embodiment and the accompanying drawings in which.

Although the specific features of the embodiments herein are shown in some drawings and not in others. This is done for convenience only as each feature may be combined with any or all of the other features in accordance with the embodiment herein.

DETAILED DESCRIPTION OF THE EMBODIMENTS HEREIN

Vial

Figure 1:
FIG. 1 illustrates a 3D image of such a vial device, according to an embodiment herein.

In FIG. 1, a 3D image of such a vial is shown. For easy observation, the vial is made of a transparent material such as glass, laminated gypsum or Plexiglas (acrylic glass). At the bottom of the vial there is a single reference point indicating the center of a circular area, wherein said area is divided into plurality of subareas and based on their distance from the said single reference point, each of said subareas represents a predefined level of growth. There are areas of various diameters marked at the bottom of the vial for estimating the level of anaerobic bacteria growth by comparing it with a given provided chart which is provided with the unit. These circles are aimed at estimating the number of anaerobic bacteria. The presence and the level of anaerobic bacteria growth is indicated by a change in the color of the medium in a circular manner and the radius of the circle formed respectively. The cap or the upper section of the device is designed in a manner that it would keep the inside of the vial completely sealed and can have a pop up or screw mechanism. Furthermore, the slide includes a sharp pointed means such as a needle which is used to carry and deliver samples of a target material into anaerobic medium.

Slide

Figure 2:
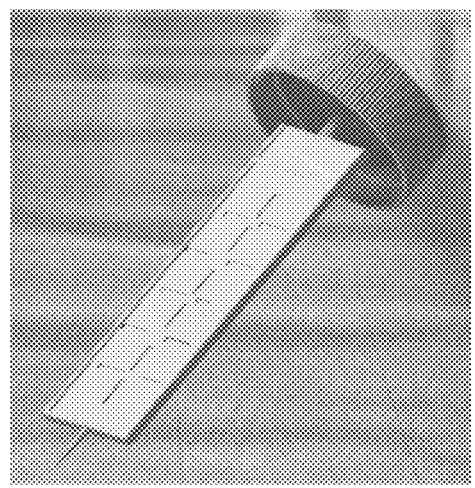
FIG. 2 illustrates a 3D image of a slide, according to an embodiment herein.

In FIG. 2, the 3D image of such a slide is shown. This slide consists of four main parts.

A side with medium for aerobic bacteria growth

A side with Medium for Fungal (yeast and mold) growth

A needle for inoculating the anaerobic bacteria

On the surface of said plurality sided slide there are build-ups to hold and prevent the medium from cracking or deformation. The medium coated on the surface of the sides of the slide could be coloured so that the colonies would be more noticeable. For example, PCA (plate count agar) is used as a medium for the aerobic bacteria growth. This medium is made of certain materials and a particular pH and has been optimized to allow growth of all types of bacteria and prevent the growth of any types of fungus. A predetermined amount of Cyclohexamide is added to the medium which will help in complete prevention of any fungal growth. Also a predetermined amount of 2,3,5-triphenyltetrazollium (TTC) can be added to the medium which will make the colour of the gram positive bacteria colonies to appear as red, so they can be seen more clearly. YM (yeast malt extract medium) which is a special medium for fungal growth is used for the fungal growth evaluation side of the slide. The components and the pH of this medium are selected and optimized in a way that it will allow the complete growth of all types of fungus such as molds and yeasts and will prevent any bacteria growth. To hinder bacteria growth and allow better growth of fungi in this medium, certain concentrations of antibiotics such as chloramphenicol, rose-bengal and streptomycine can be used. The bacterial and fungal growth media of the slide are useful in evaluation of presence of these microbes in industries such as paint, paper, pharmaceuticals, lubricant, and dairy.

Figure 3:
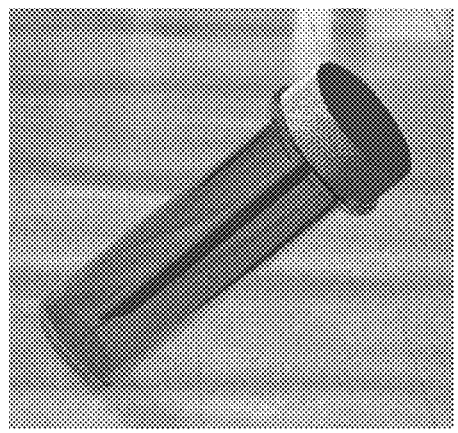
FIG. 3 illustrates a complete picture of the device including the slide and transparent vial, according to an embodiment herein.

There is a needle placed at the end of the slide. After the slide enters into the test liquid, the liquid will run to the tip of the needle and then the anaerobic medium will get inoculated by the needle entering into it. For better transformation of liquid to the tip of needle, the end of the slide can be made in a triangular or semicircular shape. The complete picture of the device including the slide and transparent vial is shown in FIG. 3.

Anaerobic Section of the Vial

The anaerobic end which is located at the bottom of the vial to evaluate the anaerobic bacteria constitutes three parts:

A medium for the growth of anaerobic bacteria
A Coating layer
An injecting needle In this part for various anaerobic bacteria, an optimized culture medium for the growth of the specific bacteria may be used. Therefore, they may be used in various industries such as food industries, dairies, pharmacy, paper, metalworking, cooling towers, paint, etc. For example, for anaerobic sulfate reducing bacteria (SRB), which can grow in paper industries, cooling towers and lubricants, leading to spoilage in the system, a TSI medium optimized in the components and pH is used. The TSI medium optimized for the SRB bacteria evaluation turn their color to black as the anaerobic bacteria grow. SRB bacteria convert the sulfate to sulfide in the absence of oxygen. The most common types of these microorganisms are *Desulfovibrio* and *Desulfotormaculum*. The sulfide freed by the bacteria reacts with the iron existing in the anaerobic medium, Forming iron sulfide, which is black in color.

After injection, the anaerobic bacteria grow in the medium in a circular form, and the number of anaerobic microbes in the medium is estimated on the basis of the growth radius and the provided chart provided. The depth of anaerobic bacteria growth medium is 1 to 20 mm thick, preferably 5 to 15 mm, and more preferably 8 to 12 mm).

Among other advantages of the present invention, is counting anaerobic, aerobic microbes and fungi with a single procedure. All the kits available in the market for counting anaerobic bacteria are all time-dependant and need to be reviewed on a daily basis, but the present invention configured to measure anaerobic, aerobic microbes and fungi within a predetermined time, for example in 48 hours.

A coating layer is used on the anaerobic medium. The layer prevents oxygen from entering the anaerobic part and leads to the creation of a completely anaerobic environment. The coating layer could comprise of paraffin wax or flexible polymers, etc. The coating layer is about 0.1 to 5 mm thick and preferably 1 to 2 mm thick.

In one embodiment of the present invention, there is a fissure in the center of the (coating layer) at the bottom of the vial where the anaerobic bacteria injection needle is placed. For testing, the slide is taken out of the vial and consequently the needle is taken out of the anaerobic bacteria growth medium, then the slide assembly is impregnated with the targeted sample, and is re-inserted in the vial which will result in impregnation of the needle into the anaerobic growth medium at the bottom of the vial and inoculating the same.

Instruction of Some Examples of Applications:

Liquids: holding the cap of the vial bring out the slide where there is bacterial and fungal growth media on its two sides in a way that there would be no contact with the agar surface. Plunge the slide into the liquid and hold it in contact for 20 to 25 seconds, so that both slides and also its end needle which is for sampling anaerobic bacteria, become thoroughly wet, shake it gently once to remove the excess fluid, return the slide to vial and close it tightly.

Semisolid: If the slide is used for emulsions or creams, sampling should be done by a sterile swab. The swab is dipped in the sample and gently rubs on the agar surface. A separate swab should be used for each side.

Solid area: Using the bendable slide, holding the slide above the targeted surfaces; pressing it down so the first area of the sides completely touches the surface area of the target; so to extract a sample of the targeted area; and inserting the slide into the vial to continue the test. Follow the same procedure for the other sides of the slide. Touch the targeted area with the needle tip for inoculating the anaerobic growth medium.

The device is put in the incubator after sampling, in a temperature of 30 to 32 degrees centigrade (if an incubator is unavailable, put it in a warm environment with the said temperatures), and the results are checked after 24 hours for bacteria (the time is to be extended until another 24 hours if no growth is observed), after 48 hours for fungi (the time is to be extended until another 24 hours if no growth is observed), and after 48 hours for SRB (the time is to be extended for another 24 hours if the medium does not become black). In case there is not a suitable warm environment and the sample is kept at room temperature (i.e. 25 degrees centigrade), another 24 hours should be added to all the above times.

Figure 4:
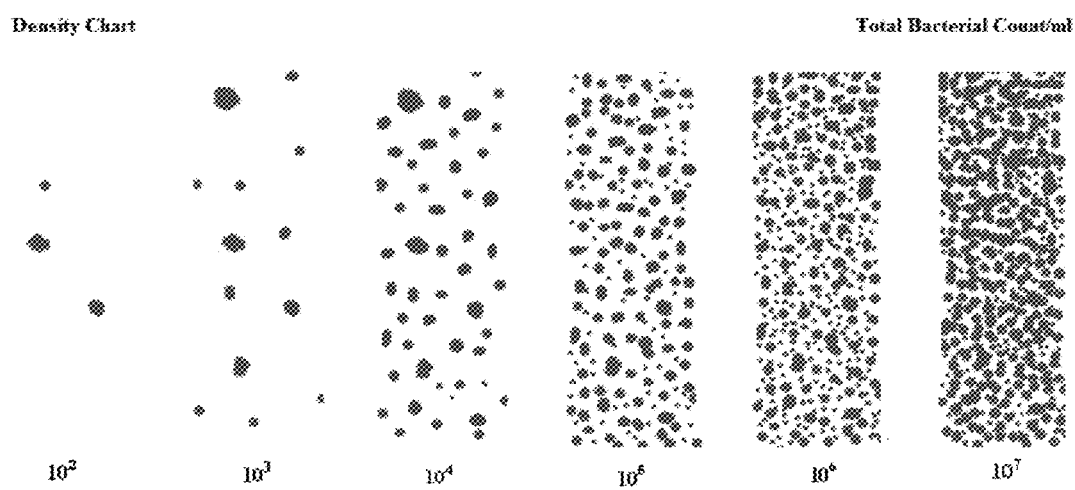
FIG. 4 illustrates a chart for counting the bacteria, according to an embodiment herein.

Total Bacterial Count:

Nearly all the aerobic bacteria will grow on the side special for aerobic bacteria, which have been made in a way to prevent the fungi growth. In this test, the size of the colonies to be formed is not important, but the number is of interest. If the surface special for bacteria growth is fully covered with bacteria, the sample should be diluted and the test be conducted by the diluted sample, so that we can have a benchmark for the extent of contamination with bacteria in the medium. This generally occurs in liquid mediums. The sample is diluted with a sterile serum (0.9 sodium chloride) by a one to ten proportion (9 milliliter of the sterile serum is used per milliliter of the solution). The medium has been synthesized in a way that most of the gram negative bacteria colonies appear in red; however, if any colony happens to appear in a color other than red it should also be taken into account in counting and estimating the number of bacteria. Note that if only one colony appears it means 102 CFU/ml, and should no colony forms, it means less than 102 CFU/ml. The chart for counting the bacteria is given in FIG. 4.

Figure 5:
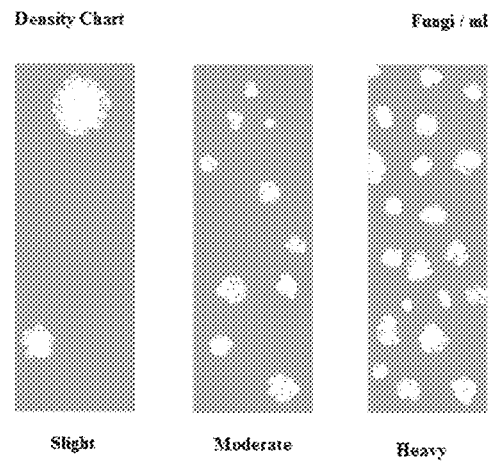
FIG. 5 illustrates a chart for yeast estimation, according to an embodiment herein.

Counting Molds and Yeasts:

Nearly all types of molds and yeasts grow on the side dedicated for fungi; the side is made so as to prevent the growth of bacteria on the medium. The yeast colonies are generally white, or accompanied by a tint of pink. Determination of the presence of yeasts is similar to bacteria; if even one colony forms, it means 102 CFU/ml, and if no colony form, it will be considered as less than 102 CFU/ml. The chart for yeast estimation is given in FIG. 5.

Figure 6:
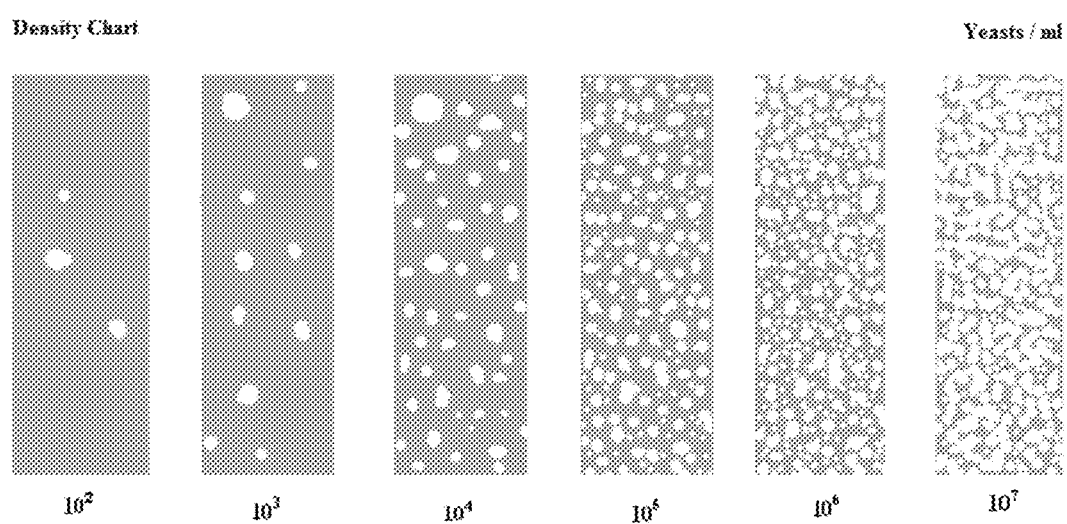
FIG. 6 illustrates a chart for fungi estimation, according to an embodiment herein.

The fungi growth is in white, green, brown and black. There is no quantitative measurement of molds. Therefore, its chart has three levels of growth: slight, moderate and heavy. The chart for fungi estimation is given in FIG. 6.

Figure 7:
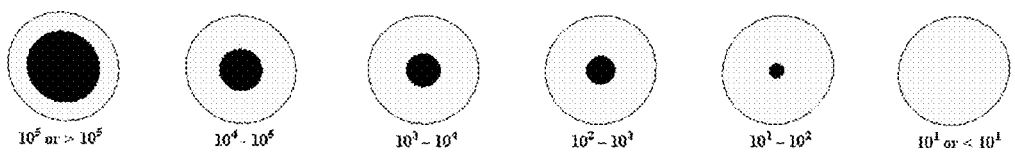
FIG. 7 illustrates a chart for estimation and counting of SRB anaerobic bacteria, according to an embodiment herein.

Counting Anaerobic Bacteria:

The level of anaerobic bacteria in a contaminated medium is estimated on the basis of the length of the formed circle diameter. As mentioned before, the shift in color for SRB anaerobic bacteria is black. In 48 to 72 hours after the start of the test, we observe the circles formation at the bottom of the vial and compare them with the provided chart to estimate the number of anaerobic bacteria growth. The chart for estimation and counting of SRB anaerobic bacteria is given in FIG. 7.

Figure 8:
FIG. 8 illustrates a photo of the lab sample of the anaerobic part, according to an embodiment herein.

The photo of the lab sample of the anaerobic part is given in FIG. 8.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments, which as a matter of language might be said to fall there between.

I claim:

1. A device for detecting aerobic bacteria, anaerobic bacteria and fungi in a targeted material which comprises of a plurality sided slide, and a vial, wherein a first side of said plurality sided slide is coated with a first predetermined medium for aerobic bacteria growth and a second side of said plurality sided slide is coated with a second predetermined medium for fungal (mold and yeast) growth, and wherein at the bottom of said vial a third predetermined medium is embedded to determine a level of presence of anaerobic bacteria; and wherein the slide comprises a needle, wherein said needle is used to carry and deliver samples of a target material into an anaerobic medium.

2. The device as claimed in claim 1, wherein said slide further comprises a sealing cap to seal the vial to prevent any contamination before and after its use.

3. The device as claimed in claim 1, wherein said vial comprises an opening area for inserting said slide.

4. The device as claimed in claim 1, wherein said second side is coated with medium for molds and yeasts growth, wherein said medium is yeast malt extract medium and wherein said medium also comprises antibiotics such as chloramphenicol, rose-bengal and streptomycin.

5. The device as claimed in claim 1, wherein said first side is coated with medium for aerobic bacteria growth, wherein said medium is plate count agar, and wherein said medium is added with a predetermined amount of a cyclohexamide and a predetermined amount of 2,3,5-triphenyltetrazollium.

6. The device as claimed in claim 1, wherein said vial contains a special medium for SRB bacteria.

7. The device as claimed in claim 6, wherein medium is deposited at the bottom of the vial, and wherein a predetermined amount of paraffin wax or flexible polymers is deposited on top of said medium to create an anaerobic environment.

8. The device as claimed in claim 7, wherein said device configured to estimate the number of anaerobic bacteria by detecting changes of attributes comprising colors at the bottom of the vial.

9. The device as claimed in claim 1, wherein said device is configured to estimated level of yeasts by comparing a number of colonies grown on the second side for fungi with a first chart provided for yeasts.

10. The device as claimed in claim 1, wherein said device is configured to estimated level of mold by comparing a number of colonies grown on the second side with a second chart provided for mold.

11. The device as claimed in claim 1, wherein said device is configured to estimated level of aerobic bacteria by comparing a number of colonies grown on the first side with a third chart provided for aerobic bacteria.

12. The device as claimed in claim 1, wherein said plurality sided slide comprises geometrical lumps on the sides of the slide to prevent medium from detaching and cracking.

13. The device as claimed in claim 1, wherein the device is configured to detect different strains of microorganisms in different environments by altering the medium, wherein the microorganisms include aerobic bacteria, anaerobic bacteria and fungi.

* * * * *